(12) United States Patent
Conrad

(10) Patent No.: US 11,690,966 B2
(45) Date of Patent: Jul. 4, 2023

(54) TRACHEOTOMY TUBE-BASED MONITORING SYSTEMS AND METHODS

(71) Applicant: The Regents of the University of California, Oakland, CA (US)

(72) Inventor: David Conrad, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 740 days.

(21) Appl. No.: 16/334,084

(22) PCT Filed: Sep. 29, 2017

(86) PCT No.: PCT/US2017/054287
§ 371 (c)(1),
(2) Date: Mar. 18, 2019

(87) PCT Pub. No.: WO2018/064471
PCT Pub. Date: Apr. 5, 2018

(65) Prior Publication Data
US 2019/0232004 A1     Aug. 1, 2019

Related U.S. Application Data

(60) Provisional application No. 62/401,511, filed on Sep. 29, 2016.

(51) Int. Cl.
*A61M 16/00* (2006.01)
*A61M 16/04* (2006.01)
(Continued)

(52) U.S. Cl.
CPC ....... *A61M 16/022* (2017.08); *A61B 5/02416* (2013.01); *A61B 5/0533* (2013.01); *A61B 5/113* (2013.01); *A61B 5/6865* (2013.01); *A61B 7/003* (2013.01); *A61M 16/04* (2013.01); *A61M 16/0411* (2014.02); *A61B 5/0816* (2013.01); *A61M 16/0497* (2013.01);
(Continued)

(58) Field of Classification Search
CPC .... A61M 16/00; A61M 16/022; A61M 16/04; A61M 16/0402; A61M 16/0468; A61M 16/0051; A61M 16/0465–0472; A61B 5/25; A61B 5/0533
See application file for complete search history.

(56) References Cited

U.S. PATENT DOCUMENTS 3,595,228 A * 7/1971 Simon ................. A61M 16/021
340/687
4,259,965 A * 4/1981 Fukuda ..................... A61B 5/25
600/395
(Continued)

OTHER PUBLICATIONS

International Search Report for PCT/US2017/054287 dated Jan. 4, 2018.
"Tracheostomy Care" (UPMC) Aug. 2007.

*Primary Examiner* — Joseph D. Boecker
*Assistant Examiner* — Thomas W Greig
(74) *Attorney, Agent, or Firm* — Thomas Horstemeyer, LLC

(57) ABSTRACT

In one embodiment, a monitoring system includes a monitoring device configured to removably attach to a tracheotomy tube, the monitoring device including a skin sensor configured to detect contact with skin of a patient's neck.

20 Claims, 4 Drawing Sheets

(51) Int. Cl.
 *A61B 5/00* (2006.01)
 *A61B 7/00* (2006.01)
 *A61B 5/024* (2006.01)
 *A61B 5/0533* (2021.01)
 *A61B 5/113* (2006.01)
 *A61B 5/08* (2006.01)

(52) U.S. Cl.
 CPC . *A61M 2205/13* (2013.01); *A61M 2205/3313* (2013.01); *A61M 2205/3375* (2013.01); *A61M 2205/3569* (2013.01); *A61M 2205/3592* (2013.01); *A61M 2205/50* (2013.01); *A61M 2205/581* (2013.01); *A61M 2205/583* (2013.01); *A61M 2205/8206* (2013.01); *A61M 2230/06* (2013.01); *A61M 2230/202* (2013.01); *A61M 2230/42* (2013.01); *A61M 2230/50* (2013.01); *A61M 2230/63* (2013.01); *A61M 2230/65* (2013.01)

(56) References Cited

U.S. PATENT DOCUMENTS

| | | | | |
|---|---|---|---|---|
| 4,306,567 | A | | 12/1981 | Krasner |
| 4,561,746 | A | * | 12/1985 | Matsuda ............... G02B 7/32 396/102 |
| 4,651,746 | A | * | 3/1987 | Wall ................ A61M 16/0096 600/483 |
| 5,070,321 | A | * | 12/1991 | Einhorn ............... A61B 5/0878 600/537 |
| 5,367,292 | A | * | 11/1994 | Szoke ................ A61B 5/0878 600/529 |
| 6,851,427 | B1 | * | 2/2005 | Nashed ............. A61M 16/0816 128/207.14 |
| 7,416,532 | B1 | * | 8/2008 | Broshears ......... A61M 16/0465 600/549 |
| 9,788,583 | B1 | * | 10/2017 | Owens .............. A41D 13/1245 |
| 2002/0115936 | A1 | * | 8/2002 | Koblanski ........... A61B 5/0205 600/481 |
| 2008/0178882 | A1 | * | 7/2008 | Christopher ...... A61M 16/0465 128/204.23 |
| 2010/0030044 | A1 | | 2/2010 | Kenowski |
| 2010/0240982 | A1 | * | 9/2010 | Westbrook .......... A61B 5/6831 600/391 |
| 2011/0197885 | A1 | * | 8/2011 | Wondka ........... A61M 16/0475 128/204.22 |
| 2012/0184799 | A1 | * | 7/2012 | Harrison .............. A61N 2/004 600/12 |
| 2014/0238398 | A1 | * | 8/2014 | Christopher ...... A61M 16/0816 128/204.22 |
| 2014/0283829 | A1 | | 9/2014 | Miller |
| 2014/0318535 | A1 | * | 10/2014 | Bullock ............. A61M 16/101 128/203.14 |

* cited by examiner

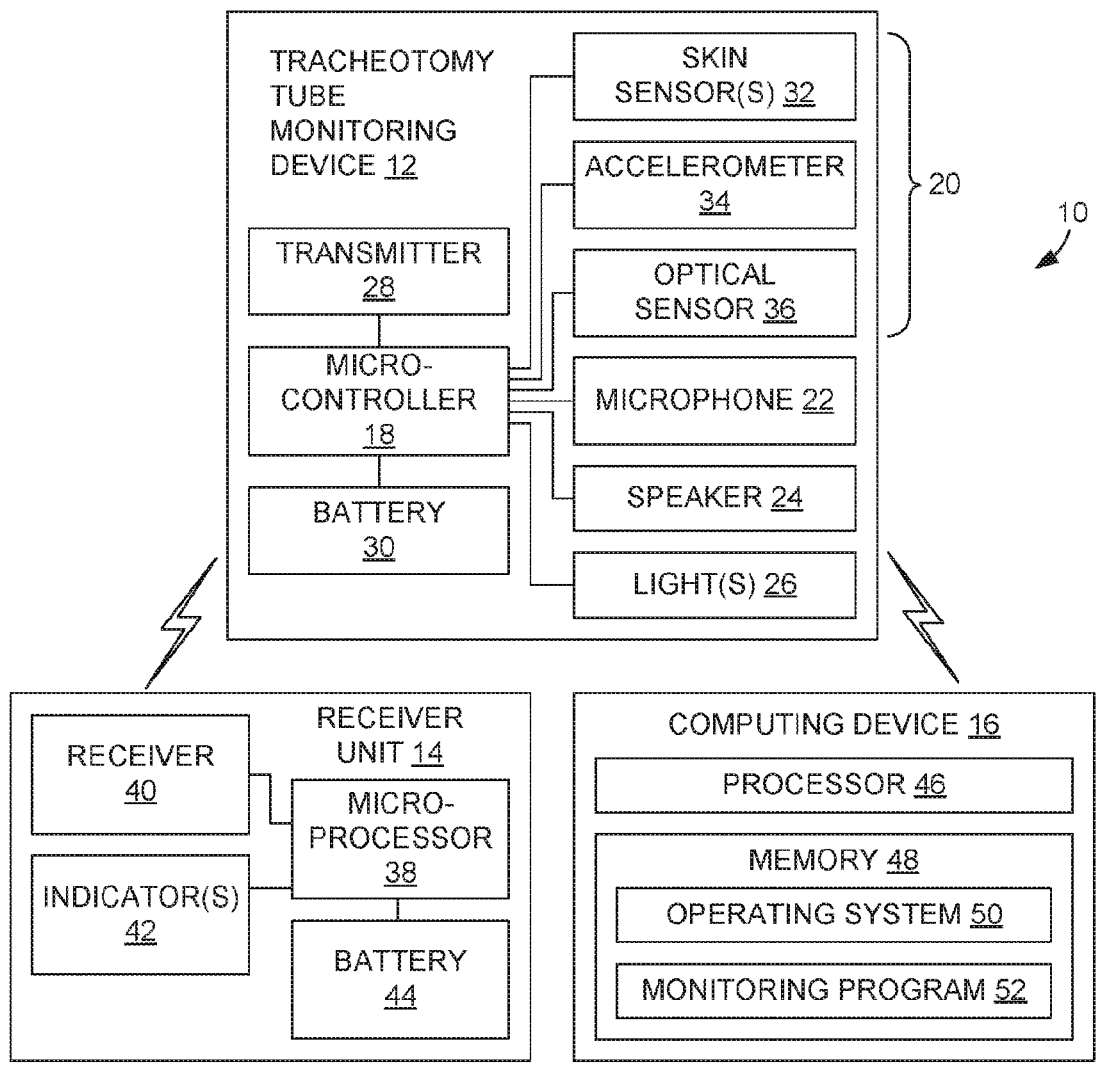
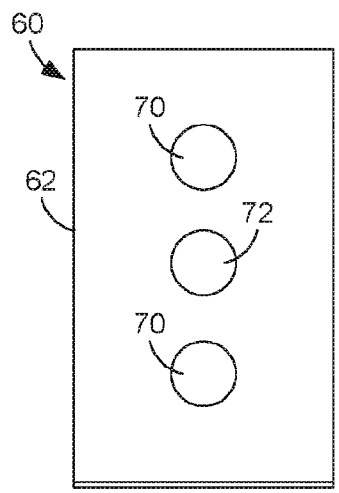
FIG. 2
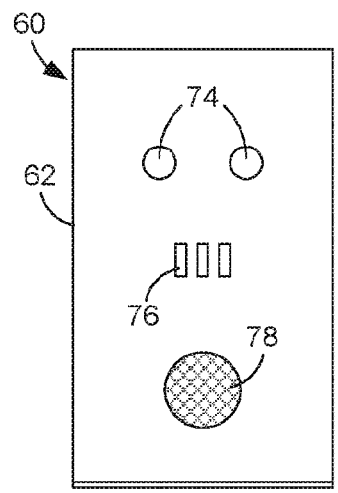
FIG. 3
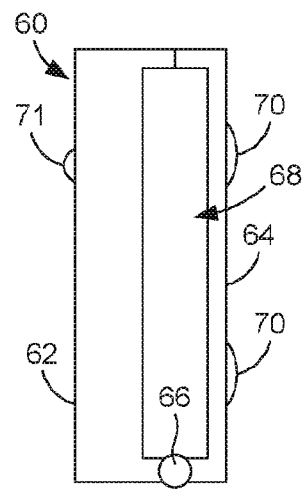
FIG. 4

TRACHEOTOMY TUBE-BASED MONITORING SYSTEMS AND METHODS

CROSS-REFERENCE TO RELATED APPLICATIONS

This application is the 35 U.S.C. § 371 national stage application of PCT Application No. PCT/US2017/054287, filed Sep. 29, 2017, where the PCT claims the benefit of and priority to U.S. Provisional Application Ser. No. 62/401,511, filed Sep. 29, 2016, both of which are herein incorporated by reference in their entireties.

BACKGROUND

Tracheotomy procedures, in which a passageway is formed through an incision in the neck to create an airway, are very common. When a tracheotomy is performed, a tracheotomy tube is typically passed through the passageway to maintain its patency and provide a secure airway.

A common concern with tracheotomies and tracheotomy tubes is that the tube will become dislodged, normally by accident. Such dislodgement can range in severity from the tube shifting out of position and creating an air leak between the tube and the passageway to the tube becoming completely removed from the passageway. Both situations pose a health risk to the patient and, potentially, a risk of death. In more stable patients, tracheotomy tube dislodgement may go unrecognized for a period of time, making it more difficult to replace the tube as the stoma begins to close.

Given that tracheotomy tube dislodgement may go unrecognized and that tube replacement is time-sensitive, it is beneficial to have a means for monitoring the placement of the tracheotomy tube so that others (hospital staff, care givers, etc.) can be alerted when the tube is out of position. Although many ventilators are configured to generate an alert if a tracheotomy tube to which the ventilator is connected is not properly positioned on the patient, tracheotomy tubes are often used independent of a ventilator and, in such situations, no alert is generated when the tube becomes dislodged.

From the above discussion, it can be appreciated that it would be desirable to have a monitoring system or method that can detect tracheotomy tube dislodgement independent of a ventilator.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 1 is a block diagram of an embodiment of a tracheotomy tube-based monitoring system.

FIG. 2 is an inner side view of an embodiment of a tracheotomy tube monitoring device of the system of FIG. 1.

FIG. 3 is an outer side view of the monitoring device of FIG. 2.

FIG. 4 is a lateral side view of the monitoring device of FIG. 2.

DETAILED DESCRIPTION

Figure 5:
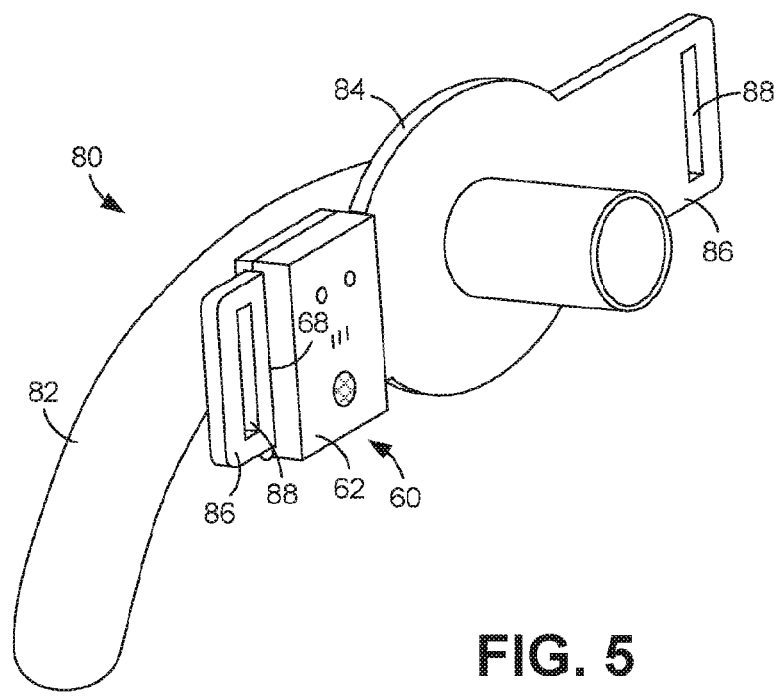
FIG. 5 is a perspective view of a tracheotomy tube having the monitoring device of FIGS. 2-4 attached thereto.

As described above, it would be desirable to have a system or method for monitoring tracheotomy tube placement independent of a ventilator. Disclosed herein are embodiments of tracheotomy tube-based monitoring systems and methods that can be used to monitor tracheotomy tube placement, as well as other patient parameters. In some embodiments, a monitoring system includes a separate and detachable monitoring device configured to attach to a flange of a tracheotomy tube. The monitoring device includes one or more sensors that can detect when they are in or out of contact with the skin of the patient's neck. When the sensors lose contact with the neck, the tracheotomy tube is out of position and others are notified. In some embodiments, the monitoring device emits an audible and/or visual alert and also wirelessly transmits an alert signal to another device, which can generate its own audible and/or visual alert that notifies one or more persons of this occurrence. In some embodiments, the monitoring device also includes other sensors that monitor various patient physical parameters that are indicative of the patient's condition.

In the following disclosure, various specific embodiments are described. It is to be understood that those embodiments are example implementations of the disclosed inventions and that alternative embodiments are possible. All such embodiments are intended to fall within the scope of this disclosure.

FIG. 1 is a block diagram of an embodiment of a tracheotomy tube-based monitoring system 10. As shown in the figure, the system 10 generally includes a tracheotomy tube monitoring device 12 and one or more other devices that can communicate with the monitoring device. In the example of FIG. 1, these other devices include a receiver unit 14 and a computing device 16.

The monitoring device 12 is configured to be removably attached to a tracheotomy tube. In some embodiments, the monitoring device 12 is configured to be removably attached to a flange of the tracheotomy tube. As shown in FIG. 1, the monitoring device 12 can include a microcontroller 18, one or more sensors 20, a microphone 22, a speaker 24, one or more indicator lights 26, a wireless transmitter 28, and a battery 30. The microcontroller 18 is configured to control overall operation of the monitoring device 12, including collecting data from the sensors 20 and performing various actions based upon the collected data. In some embodiments, the microcontroller 18 includes a microprocessor and memory (i.e., a non-transitory computer-readable medium) that stores software and/or firmware that is executed to control device operation.

As indicated in FIG. 1, the sensors 20 can comprise a variety of individual sensors. In the illustrated embodiment, the sensors 20 include one or more skin sensors 32, an accelerometer 34, and an optical sensor 36. The skin sensors 32 are configured to sense contact with the patient's neck, which is indicative of proper positioning of the tracheotomy tube. In some embodiments, the skin sensors 32 are galvanic skin response (GSR) sensors that are configured to sense the electrical conductivity of the skin of the patient's neck.

The accelerometer 34 is configured to sense vibrations transmitted by the tracheotomy tube. Such vibrations include those associated with patient breathing as well as occurrences that may be indicative of a problem, such as coughing, choking, or gagging. Furthermore, the accelerometer 34 can sense the vibrations associated with the presence of an obstruction within the tube, such as a mucus plug.

The optical sensor 36 is configured to sense, and therefore monitor, patient physical parameters, such as vital signs like heart rate, respiration rate, body temperature, and blood oxygen saturation. In some embodiments, the optical sensor 36 comprises a light source, such as an infrared (IR), red, or green light-emitting diode (LED), that emits light into the skin, as well as a light detector, such as a photodetector, that receives light reflected back from the skin. Notably, the optical sensor 36 can further be used to detect contact, or lack of contact, with the skin and, therefore, can provide redundancy to the skin sensors 32.

Although not identified in FIG. 1 as comprising one of the sensors 20, the microphone 22 can also be used as a type of sensor as it can sense sound waves that are indicative of patient breathing, coughing, choking, or gagging. In addition, the microphone 22 can function as an input device that receives voice commands that can be used to control operation of the monitoring device 12. Such commands can, for example, include commands to turn the device on or off and commands to cancel an alert generated by the device 12 using the speaker 24 and/or lights 26.

The one or more indicator lights 26, which may also comprise LEDs, can be used to convey various information to hospital staff or another caregiver of the patient. This information can include the status of the device (e.g., on or off) and the condition of the battery 30. In addition, the lights 26, along with the speaker 24, can be used to convey a problem condition.

The wireless transmitter 28 can comprise a radio frequency (RF) transmitter that is configured to transmit data via an appropriate standard, such as Bluetooth or Wi-Fi, to another device, such as the receiver unit 14 and/or the computing device 16. This data can comprise physical parameters collected by one or more of the sensors 20 as well as problem conditions detected by one or more of the sensors.

The battery 30 can comprise a disposable or rechargeable battery. Although not shown in FIG. 1, the monitoring device 12 can further include one or more user input devices, such as buttons, which can be used to control operation of the device, such as turning the device on and off as well as canceling alerts.

The data collected by the sensors 20 and the microphone 22 can be received and processed by the software and/or firmware stored within the microcontroller 18 to determine what action, if any, is necessary. For example, the microcontroller 18 can simply transmit received patient physical parameters, such as heart rate, respiration rate, body temperature, and blood oxygen saturation, to the receiver unit 14 and/or the computing device 16 for presentation to a user of those devices. In addition, the software and/or firmware stored within the microcontroller 18 can analyze the collected data to determine if there is a problem and, if so, whether or not an alert should be generated. For example, if the one or more skin sensors 32 lose contact with the skin, the microcontroller 18 can activate the speaker 24 and the lights 26 to sound an alert and flash, respectively. In addition, the microcontroller 18 can transmit an alert signal to the receiver unit 14 and/or the computing device 16 so that similar alerts can be generated by those devices. As another example, if the received accelerometer data indicates that the patient is choking, similar alerts and transmissions can be generated.

With further reference to FIG. 1, the receiver unit 14 is an independent device that can be placed in a location in which a person responsible for the patient, such as hospital staff or another caregiver, can hear and/or see an alert generated by the unit. In the illustrated embodiment, the unit 14 includes a microcontroller 38, a wireless receiver 40, one or more indicators 42, and a battery 44. The microcontroller 38 is configured to control operation of the unit 14, the wireless receiver 40 is configured to receive RF signals transmitted by the monitoring device 12, and the indicators 42 are configured to generate the alerts. The indicators 42 can include one or more lights and/or one or more speakers adapted for this purpose. Although a battery 44 is shown in FIG. 1, the unit 14 can, alternatively, be powered by another power source, such as a wall outlet.

The computing device 16 can comprise any device that is configured to receive communications from the monitoring device 12, convey monitored patient physical parameters, and generate alerts responsive to problem conditions. By way of example, the computing device 16 can comprise a desktop computer, a notebook computer, a tablet computer, a smart phone, or any other device with sufficient computing capabilities. As shown in FIG. 1, the computing device 16 includes a processor 46 and memory 48 (i.e., a non-transitory computer-readable medium) that stores an operating system 50 and a monitoring program 52, which is a software program or application configured to receive and process the data transmitted from the monitoring device 12. As patient physical parameters are received, they can be stored and presented to a user by the program 52 for monitoring purposes. In addition, the program 52 can, like the software/firmware of the monitoring device 12, analyze the collected data to determine whether or not an alert should be generated.

FIGS. 2-4 illustrate an example design for the monitoring device 12. As shown in these figures, a monitoring device 60 includes a waterproof outer housing 62 that encloses various electronic components of the device, such as the microcontroller, the accelerometer, transmitter, and battery. As shown in FIG. 4, the monitoring device 60 can, in some embodiments, include a clamp element 64 that can be used to attach the device to a tracheotomy tube. In the illustrated example, the clamp element 64 connects to the housing 62 at one end with a hinge 66 that enables the element to pivot between a closed position shown in FIG. 4 and an open position. A secure closure, such as a locking element, can be provided at the other end of the clamp element 64 to maintain the clamp element in the closed position. In some embodiments, such a locking element can be mechanical or magnetic. As illustrated in FIG. 4, the housing 62 and the clamp element 64 together define an opening 68 that is configured to receive a flange of the tracheotomy tube. However, it is noted that, in alternative embodiments, the monitoring device 60 can omit the clamp element 64 and instead comprise a housing 62 that includes the opening 68 for cases in which the device is to be slid into place over the tracheotomy tube flange (see FIGS. 7 and 10).

As shown in FIGS. 2 and 4, the monitoring device 60 includes two skin sensors 70, one provided near a top end of the device and one provided near the bottom end of the device. In addition, the monitoring device 60 includes an optical sensor 72, which can be positioned between the two skin sensors 70. As shown in FIG. 3, the monitoring device 60 further includes multiple lights 74, a microphone 76, and a speaker 78.

Figure 6:
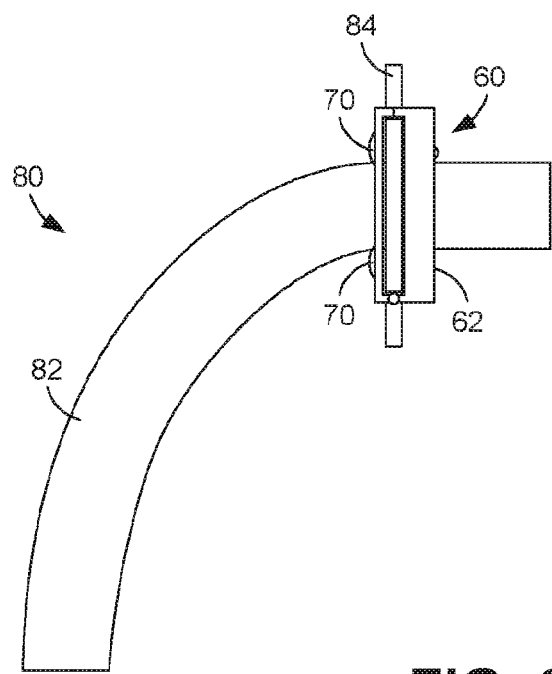
FIG. 6 is a side view of the tracheotomy tube and monitoring device shown in FIG. 5.

FIGS. 5 and 6 illustrate the monitoring device 60 attached to a tracheotomy tube 80. As shown in these figures, the tracheotomy tube 80 includes a lumen 82 that is adapted for insertion into the trachea and a flange 84 that is adapted to abut the neck and secure the tube to the patient. The flange 84 comprises lateral portions (wings) 86 that include openings 88 through which a band, tracheotomy tube collar, or tie can pass. The band, collar, or tie can be wrapped around the back of the patient's neck and secured the tracheotomy tube 80 to keep it in position.

As shown in FIG. 5, the monitoring device 60 is attached to one of the lateral portions 86 of the tube flange 84. In particular, the lateral portion 86 is received within the opening 88 of the monitoring device 12 such that the device wraps around the lateral portion. As shown in the figures, the monitoring device 60 is attached to the flange 84 such that the inner side of the device, which incorporates the sensors 70, faces the patient when the tracheotomy tube 80 is in use. More particularly, when the tracheotomy tube 80 is properly inserted into the trachea, the sensors 70 will be placed in positive contact with the skin of the neck surrounding the tracheostomy.

When the monitoring device 12 is to be used, it can be attached to the tracheotomy flange 84 prior to insertion of the lumen 82. The tracheotomy tube 80 can then be properly positioned with the flange 84 in contact with the patient's neck and the sensors 70 in contact with the patient's skin. The tracheotomy tube 80 can then be fixed in place with an appropriate band, collar, or tie. The monitoring device 12 can then be turned on and used to monitor patient physical parameters and detect conditions that warrant the generation of an alert. Accordingly, the optical sensor 72 can collect data as to heart rate, respiration rate, body temperature, and blood oxygen saturation, and provide this data to the microcontroller. The microcontroller can transmit this data in real time to one or more other devices (e.g., the receiver unit 14 and/or computing device 16) as well as conduct analysis of the data. If, through such analysis, the microcontroller determines that an alert should be generated, the microcontroller can activate the lights 74 and the speaker 78 on the monitoring device 60 to alert hospital staff or other caregivers of the problem. In addition, the microcontroller can simultaneously transmit an alert signal to the other devices using the wireless transmitter.

Data can is also collected from the skin sensors 70, accelerometer, and the microphone 76 and provided to the microcontroller for analysis. Again, if the data indicates that there is a problem, such as loss of contact with the neck or difficulty breathing, the microcontroller can also activate the lights 74 and the speaker 78 on the monitoring device 60 and transmit an alert signal to the other devices. Accordingly, it can be appreciated that the monitoring device 12 is configured to collect various data concerning patient physical parameters and the status of the tracheotomy tube, and take action as necessary to ensure the safety and health of the patient. Notably, in cases in which the monitoring device 60 includes two skin sensors 70, the microcontroller can be configured to issue an alert only if both sensors lose contact with the skin.

Figure 7:
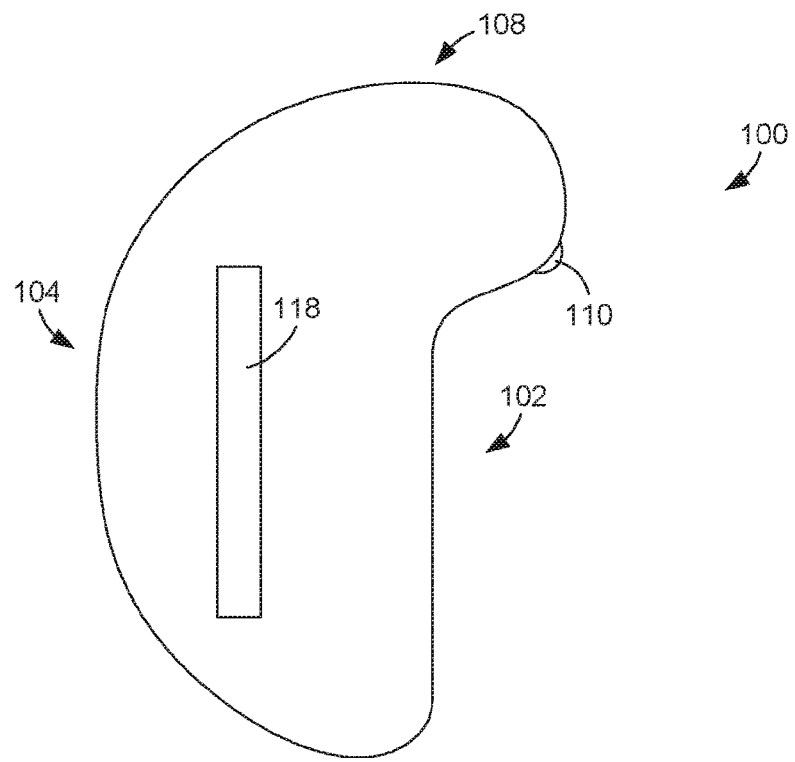
FIG. 7 is a lateral side view of a further embodiment of a tracheotomy tube monitoring device.
Figures 8, 9:
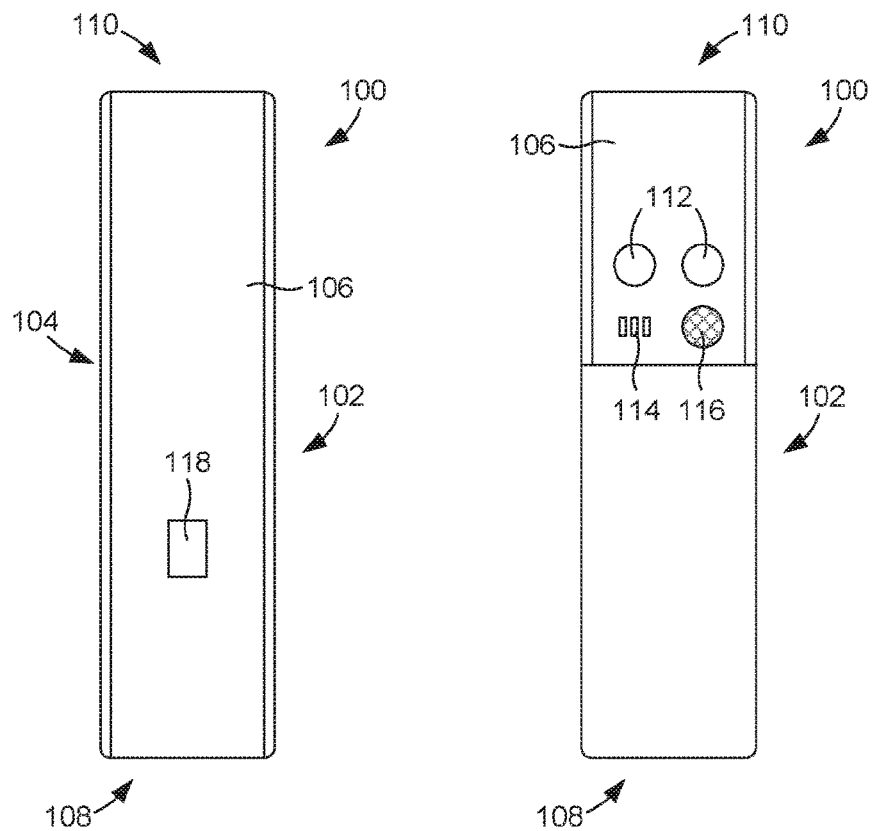
FIG. 8 is an inner side view of the monitoring device of FIG. 7.
FIG. 9 is an outer side view of the monitoring device of FIG. 7.

FIGS. 7-9 illustrate an alternative design for the monitoring device 12. As shown in these figures, a monitoring device 100 comprises an outer housing 102 that is generally kidney shaped (when viewed from the side). This shape results in an inner side 104 of the housing 102 that faces the patient forming a convex curve that follows the contours of the patient's neck when the monitoring device is in use. Like the monitoring device 60, the monitoring device 100 includes a skin sensor. In this embodiment, however, the skin sensor comprises a continuous conductive strip 106 that, as is apparent from FIGS. 8 and 9, begins at the bottom end 108 of the housing 102, extends along the full length of the inner side 104 of the housing, and further wraps around the top end 110 of the housing. The conductive strip 106 can, in some embodiments, comprise a continuous strip of metal that is mounted to the housing 102. Because it extends along the entire inner side 104 and top end 110 of the monitoring device 100, the skin sensor 106 has a better likelihood of remaining in contact with the skin of the patient and, therefore, reduces the likelihood of false positive indications of tube dislodgement. In addition, the curved design of the housing 102 may be more comfortable to the patient.

As is indicated in FIGS. 7 and 9, the monitoring device 100 also includes lights 112, a microphone 114, and a speaker 116. As indicated in FIG. 8, an optical sensor 118 can be provided within the skin sensor 106 on the inner side 104 of the housing 102 so as to be positioned to contact the patient's skin during use of the monitoring device 100. With reference back to FIG. 7, the housing 102 also includes an opening 119 that is configured to receive an extension of a tracheotomy tube flange.

Figure 10:
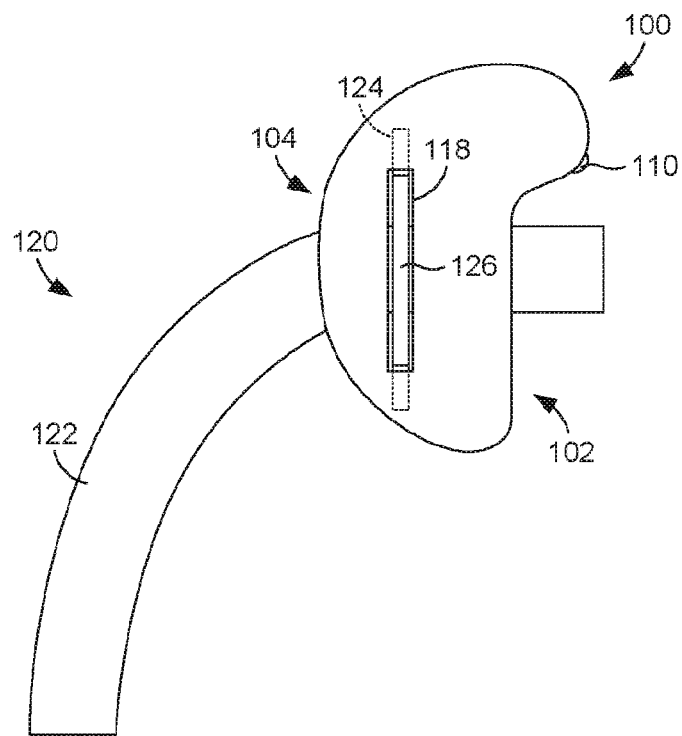
FIG. 10 is a perspective view of a tracheotomy tube having the monitoring device of FIGS. 7-9 attached thereto.

FIG. 10 illustrates the monitoring device 100 attached to a tracheotomy tube 120. As shown in this figure, the tracheotomy tube 120, like tube 80, includes a lumen 122 and a flange 124 that comprises lateral portions 126. One lateral portion 126 is received within the opening 119 of the monitoring device 100 such that the device wraps around the lateral portion and the inner side 104 of the device faces the patient when the tracheotomy tube 120 is in use and the sensors 106 and 118 make positive contact with the patient's skin.

The invention claimed is:

1. A monitoring system for monitoring placement of a tracheotomy tube that has been passed through a tracheostomy formed in the neck of a patient, the system comprising:
a monitoring device configured to directly and removably attach to the tracheotomy tube, the monitoring device including a skin sensor solely configured to detect the electrical conductivity of the skin of the patient's neck and, therefore, detect whether the sensor is or is not in direct contact with skin of a patient's neck, wherein the tracheotomy tube is correctly placed when such direct contact is detected.

2. The monitoring system of claim 1, wherein the monitoring device is configured to directly and removably attach to a flange of the tracheotomy tube.

3. The monitoring system of claim 2, wherein the monitoring device is configured to directly and removably attach to a lateral portion of the flange.

4. The monitoring system of claim 3, wherein the skin sensor is a galvanic skin response sensor.

5. The monitoring system of claim 1, wherein the monitoring device further includes an accelerometer configured to sense vibrations transmitted by the tracheotomy tube.

6. The monitoring system of claim 1, wherein the monitoring device further includes an optical sensor configured to sense patient physical parameters.

7. The monitoring system of claim 6, wherein the patient physical parameters include one or more of heart rate, respiration rate, body temperature, and blood oxygen saturation.

8. The monitoring system of claim 1, wherein the monitoring device further includes a microphone configured to sense sound waves that are indicative of patient breathing, coughing, choking, or gagging.

9. The monitoring system of claim 1, wherein the monitoring device further includes a microcontroller that is configured to receive signals from the skin sensor and generate an alert if skin sensor indicates that it is not in direct contact with the skin.

10. The monitoring system of claim 9, wherein the monitoring device further includes a speaker and a light and wherein the microcontroller is configured to generate audible alerts that are emitted by the speaker and visual alerts that are emitted by the light.

11. The monitoring system of claim 10, wherein the monitoring device further includes a wireless transmitter and wherein the microcontroller is further configured to generate alert signals that are wirelessly transmitted to other devices using the wireless transmitter.

12. The monitoring system of claim 11, further comprising a separate device configured to receive alert signals wirelessly transmitted by the monitoring device and generate its own alerts.

13. A monitoring device for monitoring placement of a tracheotomy tube that has been passed through a tracheostomy formed in the neck of a patient, the device comprising:
    a housing configured to directly and removably attach to a flange of the tracheotomy tube such that the monitoring device is solely supported by the flange;
    a skin sensor provided on the housing that is solely configured to detect the electrical conductivity of the skin of the patient's neck and, therefore, detect whether the sensor is or is not in direct contact with skin of a patient's neck; and
    a microcontroller contained within the housing that is configured to continually receive from the skin sensor signals that indicate that the skin sensor either is or is not in direct contact with the patient's skin and to generate an alert if a signal is received from the skin sensor that indicates the skin sensor is not in direct contact with the patient's skin.

14. The monitoring device of claim 13, wherein the skin sensor is a galvanic skin response sensor.

15. The monitoring device of claim 13, further comprising an accelerometer configured to sense vibrations transmitted by the tracheotomy tube.

16. The monitoring device of claim 13, further comprising an optical sensor configured to sense patient physical parameters.

17. The monitoring device of claim 13, further comprising a microphone configured to sense sound waves that are indicative of patient breathing, coughing, choking, or gagging.

18. The monitoring device of claim 13, further comprising a speaker and a light and wherein the microcontroller is configured to generate audible alerts that are emitted the speaker and visual alerts that are emitted by the light.

19. The monitoring device of claim 13, further comprising a wireless transmitter and wherein the microcontroller is further configured to generate alert signals that are wirelessly transmitted to other devices using the wireless transmitter.

20. A method for monitoring placement of a tracheotomy tube that has been passed through a tracheostomy formed in the neck of a patient, the method comprising:
    directly and removably attaching a single integrated monitoring device to a flange of the tracheotomy tube such that the monitoring device is solely supported by the flange;
    inserting the tracheotomy tube through the tracheostomy of the patient;
    detecting whether there is direct physical contact between a skin sensor of the monitoring device and a neck of the patient, the skin sensor being solely configured to detect the electrical conductivity of the skin of the patient's neck and, therefore, detect whether the sensor is or is not in direct physical contact with skin of a patient's neck; and
    generating an alert with the monitoring device when the skin sensor senses that the sensor is not in direct physical contact with the skin of the patient's neck.

\* \* \* \* \*